United States Patent [19]

Champain

[11] Patent Number: 4,848,332
[45] Date of Patent: Jul. 18, 1989

[54] DEVICE FOR CONTROLLING THE PRESSURE OF A FLUID AND INJECTION SYSTEM FOR THIS FLUID EMPLOYING THIS DEVICE

[75] Inventor: Roger Champain, Les Loges-en-Josas, France

[73] Assignee: L'Air Liquide, Paris, France

[21] Appl. No.: 163,145

[22] Filed: Feb. 25, 1988

Related U.S. Application Data

[63] Continuation of Ser. No. 796,326, Nov. 7, 1985, abandoned.

[30] Foreign Application Priority Data

Nov. 13, 1984 [FR] France ............................... 84 17236

[51] Int. Cl.$^4$ ............................................. A61M 16/00
[52] U.S. Cl. ............................ 128/204.21; 128/204.26; 128/204.28; 73/705
[58] Field of Search ...................... 128/204.21, 204.22, 128/204.26, 204.28; 73/729, 705

[56] References Cited

U.S. PATENT DOCUMENTS

| | | | |
|---|---|---|---|
| 2,223,705 | 12/1940 | Roudnicky | 73/729 |
| 3,137,158 | 6/1964 | Krueger | 73/729 X |
| 3,502,892 | 3/1970 | Brittain | 73/705 X |
| 3,831,596 | 8/1974 | Cavallo | 128/145.5 |
| 4,289,963 | 9/1981 | Everett | 73/705 X |
| 4,599,902 | 7/1986 | Gray | 73/705 |

FOREIGN PATENT DOCUMENTS

| | | | |
|---|---|---|---|
| 2346025 | 3/1977 | France . | |
| 0021972 | 2/1978 | Japan | 73/705 |
| 2004180 | 3/1979 | United Kingdom . | |
| 2089497 | 6/1982 | United Kingdom . | |

*Primary Examiner*—William E. Wayner
*Attorney, Agent, or Firm*—Lee C. Robinson, Jr.

[57] ABSTRACT

The control device is applicable in particular in the control of the injection of oxygen in the course of an oxygen treatment through a nasal mask. The device comprises a sealed chamber (5) in which are disposed, on one hand, a very pliable bladder (6) one side of which is subjected to atmospheric pressure while the other side is subjected to the depression which must be detected, and, on the other hand, an opto-electronic sensor (7), the bladder being connected to a movable screen (9) capable of intercepting or not intercepting, depending on the state of the bladder (6) and consequently of the depression to be detected, the light beam between the light beam emitter and the receiver of the opto-electronic sensor (7).

22 Claims, 5 Drawing Sheets

DEVICE FOR CONTROLLING THE PRESSURE OF A FLUID AND INJECTION SYSTEM FOR THIS FLUID EMPLOYING THIS DEVICE

This application is a continuation of application Ser. No. 796,326, filed Nov. 7, 1985 now abandoned.

The present invention relates to a device for controlling the pressure of a fluid applicable in particular to the control of the injection of oxygen in the course of oxygen treatment with a nasal mask and a system for injecting this fluid employing such a device.

It more particularly concerns a device for controlling the pressure of a fluid delivered by a fluid source to a user through a pipe, said device being capable of delivering a signal to means controlling the flow of the fluid, and comprising a sealed chamber into which the fluid is injected by fluid injecting means, said chamber comprising a movable wall responsive to the pressure, means for interrupting the light beam of a photodetector unit which delivers a control signal to the means controlling the flow of the fluid, and means for transmitting the movement of the movable wall to the means for interrupting the light beam.

Various apparatus are known for the treatment of respiratory insufficiency of a patient which supply additional oxygen from a source through a pipe opening in the vicinity of the respiratory passages of the patient. One of the most common of these apparatus is the oxygen treatment mask which is adapted to the face and has two appendages enabling oxygen to be supplied to the two nostrils of the patient.

These apparatus are usually provided with a simple manually-controlled valve inserted in the oxygen supply conduit and opened by the patient when the apparatus is in use. Consequently, the respiratory passages of the patient are permanently supplied with oxygen both during the inhaling and exhaling phases, which results in a waste of oxygen.

To overcome this drawback, devices have been proposed based on the detection of the nasal depression in the course of the inhaling phase so as to produce the supply of oxygen only during these inhaling phases. An apparatus of this type, described in the European patent application No. 99,283, is based on the measurement of the differences in temperature between the inhaled air and the exhaled air.

In tropical countries, for example, or in a high temperature hospital environment, the differences in temperature between the inhaled and exhaled gases may be insufficient for the reliable operation of such apparatus.

An apparatus is known from the British Pat. No. 2,089,497, for controlling the pressure of a fluid delivered by a pump in which the fluid to be delivered is injected into a sealed chamber on one side of a flexible diaphragm. This flexible diaphragm is connected to a second flexible diaphragm which is connected to an arm acting on a lever whose upward movement brings about the interruption of the beam of a photodetector. The lever is maintained in the lower position by a spring which opposes the movement of the flexible diaphragm.

Such a system has several drawbacks. Its structure is complicated, which makes it costly, and its sensitivity cannot be adapted to the low differential pressures involved in oxygen treatment. The particular problem presented in this technical field is to provide devices which are responsive the very low pressure differences between atmospheric pressure and the inhaling or exhaling pressure of a patient who may be in a state of considerable weakness and cannot be expected to make great efforts to breathe.

An object of the invention is to overcome these drawbacks and to provide a device for treating respiratory deficiency of a patient of very simple and very sensitive design, whose operation is independent of temperature and which may be used with any type of oxygen treatment mask.

Accordingly, it is an object of the invention to provide a device for treating respiratory deficiency of a patient by the supply of an inhalation fluid from a source of inhalation fluid to supplement the supply of oxygen inhaled from the surrounding atmosphere by the patient comprising a first duct, means to connect one end of said first duct to said source of inhalation fluid, the other end of said first duct including first means adapted to be inserted into the patient's nostrils or mouth, valve means in said first duct adapted to control the flow of inhalation fluid through said duct from said source of inhalation fluid, a sealed chamber, a second duct, means to connect one end of said second duct to an opening of said sealed chamber, the other end of said second duct including second means to be inserted into the patient's nostrils or mouth, said chamber being at least partially filled by air to or from the patient, said sealed chamber comprising a reservoir in the form of a pliable bladder having a pressure responsive movable wall, a photodetector unit for delivering an electric signal to an electronic circuit connected to the valve, and means to control the opening or the closing of said valve means, said photodetector unit including means for emitting a light beam, means for receiving said light beam and means for intercepting the light beam dependent on said movable wall, said reservoir having an opening communicating with means for supplying air from the surrounding atmosphere, said movable wall being subjected on one side to the pressure of air from the surrounding atmosphere and on the other side to the pressure of air to or from the patient, the difference of pressure between both sides of the movable wall causing a displacement of said wall in a direction toward the lower pressure.

There will be described hereinafter by way of non-limiting examples various embodiments of the invention with reference to the accompanying drawings, in which.

Figure 1:
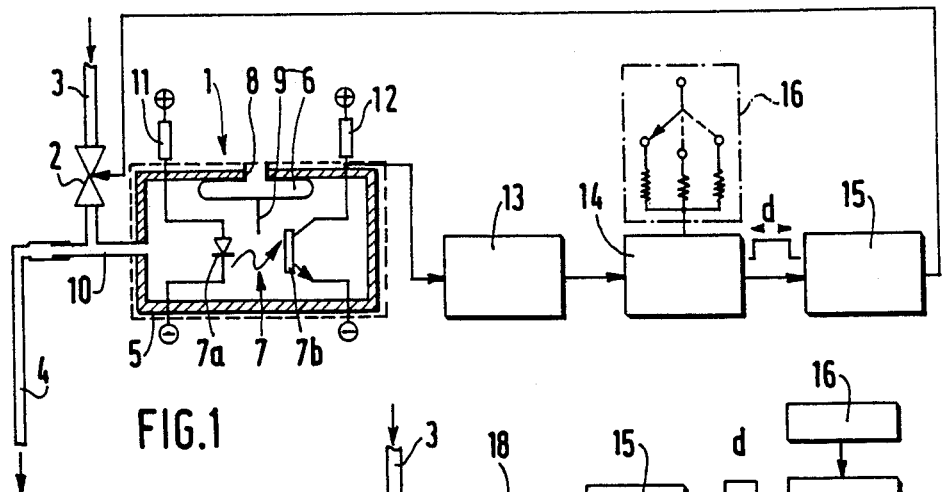
FIG. 1 is a block diagram of a detector of low depressions employed with a commercially-available treatment mask.

The depression detector shown in FIG. 1, and generally designated by the reference numeral 1, is adapted to control an electrovalve 2 inserted in an oxygen supply pipe 3 connected to an oxygen treatment mask only the end part 4 of which is shown in the drawing.

The low depression detector 1 comprises a sealed chamber 5 in which are disposed, on one hand, a very sensitive bladder 6, and, on the other hand, an opto-electronic sensor 7. The bladder 6 used in the detector according to the invention may have, for example, a diameter of 28.4 mm and a thickness of 0.2 mm and it may be composed of silicone of the type known under the name of VERSILIC 3706H manufactured by the company VERNEPET. The bladder 6 bears against a wall of the chamber 5 and its internal volume communicates with the exterior through an opening 8 provided in this wall so that the bladder 6 is subjected internally to atmospheric pressure. This bladder 6 moreover carries on its movable front side a strip 9 constituting a screen and capable of being interposed between the emitter 7a (emitting diode) and the receiver 7b (phototransistor) of the opto-electronic sensor 7. Further, the interior of the sealed chamber 5 communicates with the oxygen supply pipe 3, downstream of the valve 2, through a conduit 10.

The pliability or flexibility of the bladder must be such that a pressure variation of 1 mm of water results in a displacement of the screen of at least 0.05 mm. In practice, it is preferred to employ a bladder which has the highest possible pliability. There are currently commercially available bladders whose pliability is one the order of 0.15 mm per mm of water.

The opto-electronic sensor 7 is connected to an electronic circuit controlling the valve 2. More particularly, its emitter 7a is connected to an electric supply through a resistor 11. In the same way its receiver 7b is also connected to this electric supply 11b in series with a resistor 12, and the output signal of the opto-electronic sensor, taken from between the resistor 12 and the collector of the phototransistor 7b constituting the receiver, is applied to a shaping circuit 13. The output of this shaping circuit 13 is connected to the input of a monostable 14 whose output is connected to a circuit 5 controlling the electrovalve 2. A circuit 16 for varying the duration of the actuation of the monostable 14, i.e. the duration d of its output signal, is provided for choosing at will the duration of the oxygen inhaling phase.

The detector just described operates in the following manner: So long as the patient does not inhale, the pressure prevailing in the oxygen treatment mask 4, the conduit 10 and the interior of the chamber 5 which is due to the exhaling of the patient, is relatively high so that the bladder 6 is flattened and the screen 9 is not interposed between the emitter 7a and the receiver 7b of the opto-electronic sensor 7, which is also the case at rest. The valve 2 is maintained closed and no oxygen is supplied to the patient. Right at the start of an inhaling phase there is produced in the oxygen treatment mask 4, and consequently within the sealed chamber 5, a low depression which immediately causes the inflation of the bladder 6 so that the strip 9 constituting a screen is totally or partly interposed between the emitter 7a and the receiver 7b of the opto-electronic sensor 7 in accordance with the adjustment thereof. This sensor consequently delivers on the collector of the phototransistor 7b a pulse which is shaped by the circuit 13 and is applied to the input of the monostable 14. The latter emits at its output a trigger pulse of duration d which may be chosen as desired by means of the control circuit 15 which then causes the opening of the valve 2 for a duration d determined by the actuation time of the monostable 14. The patient thus receives, in each inhaling phase, a well-determined quantity of oxygen. At the end of the duration d, the monostable 14 returns to its position of rest and causes, through the control circuit 15, the closure of the electrovalve 2 (the case of a normally closed electrovalve which open only when the patient inhales).

Figure 2:
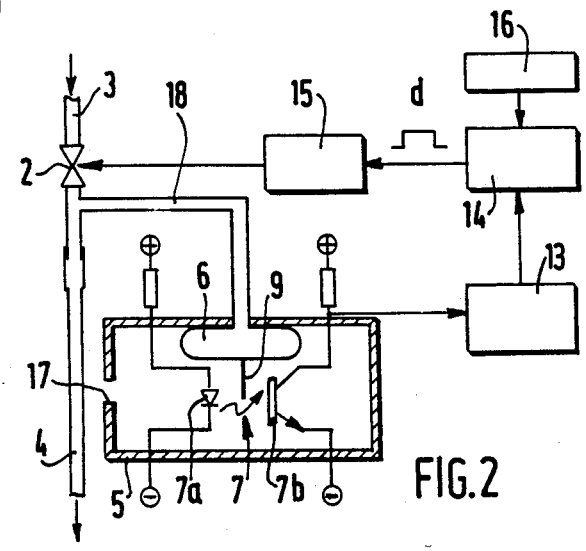
FIG. 2 is a block diagram of a modification of the low depression detector.

In the modification shown in FIG. 2, in which the same elements as those of FIG. 1 carry the same reference numerals, the interior of the chamber 5 is put into communication with the atmosphere through an opening 17 provided in one of its walls, while the interior of the bladder is connected to the oxygen supply pipe 3, downstream of the valve 2, through a conduit 18. The operation of this detector is the opposite of that previously described with reference to FIG. 1. In the state of rest, i.e. so long as atmospheric pressure prevails in the oxygen treatment mask 4, the bladder 6 is inflated and the strip constituting a screen 9 carried thereby is interposed between the emitter 7a and the receiver 7b of the opto-electronic sensor 7. On the other hand, at the beginning of each inhaling phase, the low depression appearing in the oxygen treatment mask 4 is transmitted through the conduit 18 to the interior of the bladder 6 so that the latter deflates and withdraws the screen 9. The light beam emitted by the emitter 7a is then received by the receiver 7b and this results in the delivery of a pulse and the opening of the valve 2 for a period chosen as desired by means of the circuit 16, as in the case of the embodiment shown in FIG. 1.

Figure 3:
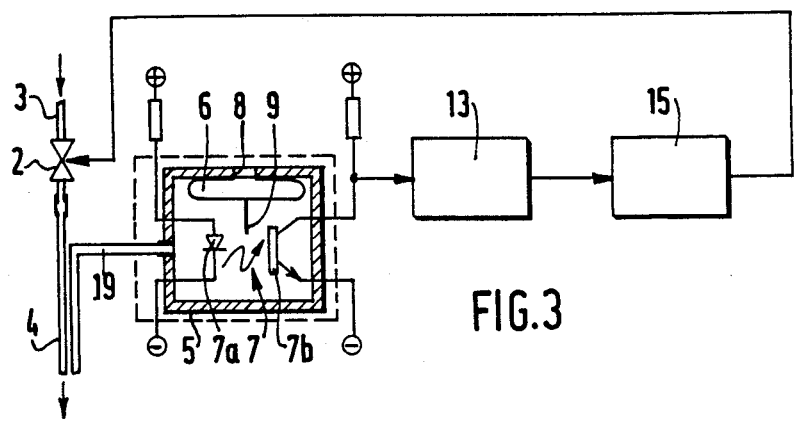
FIG. 3 is a block diagram of a depression detector which may be used in an oxygen treatment mask having an accessory pressure take-off.

FIG. 3 shows a modification of a detector used with an oxygen treatment mask 4 having an accessory pressure take-off pipe 19. This pipe 19 is connected to the interior of the sealed chamber 5, the interior of the bladder 6 being put into communication with the atmosphere, as in the case of the embodiment shown in FIG. 1. Thus, during any inhaling phase, the pressure prevailing in pipe 19 is transmitted to the interior of the sealed chamber 5 so that the bladder 6 is inflated and interposes the strip constituting a screen 9 between the emitter 7a and the receiver 7b of the opto-electronic sensor 7. The output signal of the opto-electronic sensor is shaped by the circuit 13 and applied directly to the circuit 15 controlling the electrovalve so as to maintain the electrovalve 12 permanently open throughout the duration of the inhaling phase, i.e. so long as a depression prevails in the pipe 19.

Figure 4:
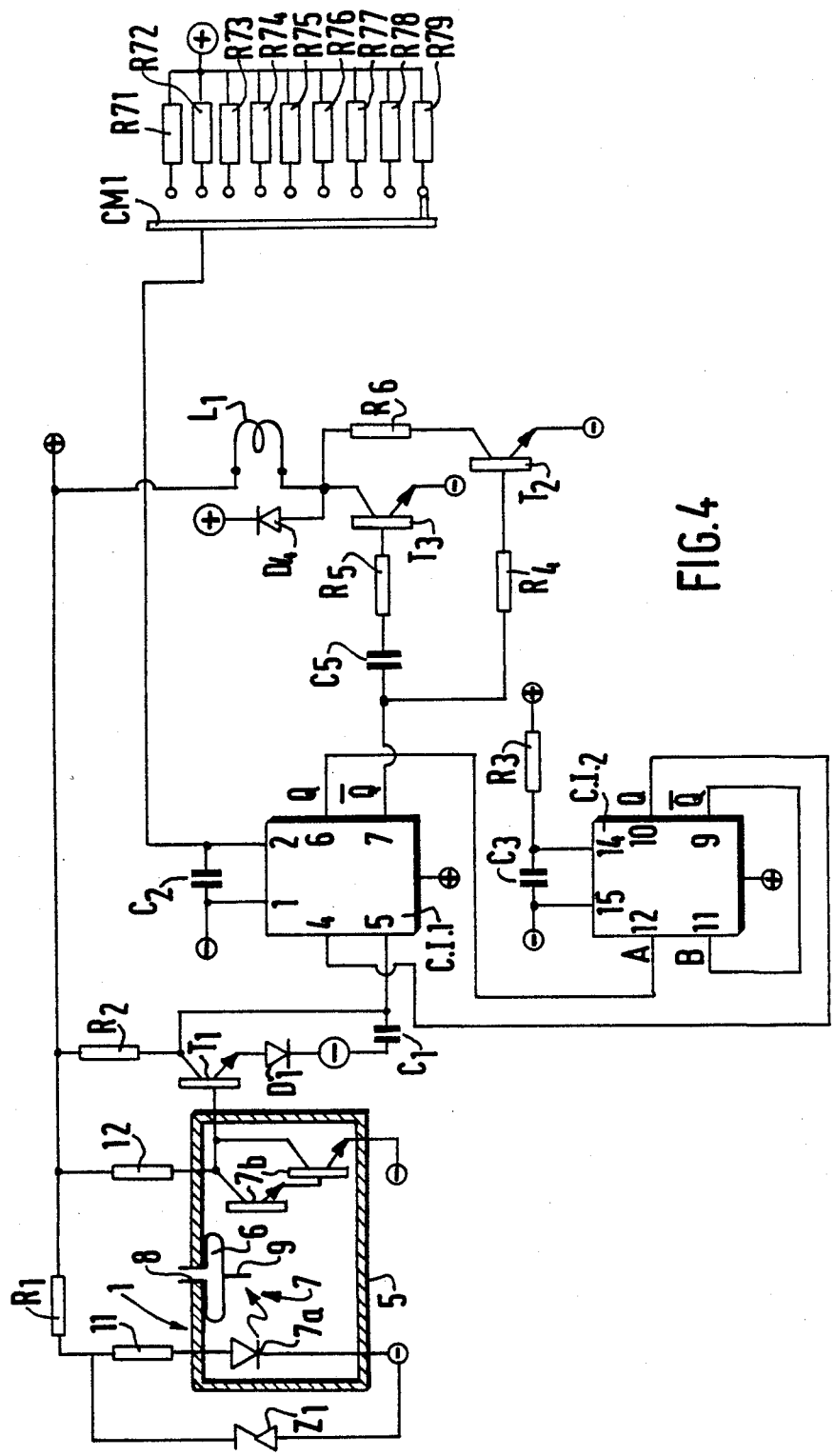
FIG. 4 is an electric diagram explaining the actuation of an electrovalve by means of the device according to the invention.

FIG. 4 discloses an electronic diagram explaining the actuation of an electrovalve by means of the device according to the invention. The sealed chamber 5 whose air supply from the patient has not been shown in the figure, comprises, as before, the opto-electronic sensor 7 formed, on one hand, by the emitter diode 7a, and, on the other hand, by the two phototransistors 7b connected in a Darlington circuit. The collector common to the two phototransistors 7b is connected through the resistor 12 to the plus terminal of the supply and the emitter of the output transistor 7b of the Darlington circuit is connected to the minus terminal of the supply. Likewise, the photodetector 7a is connected by its cathode to the minus terminal of the supply and by its anode to the plus terminal of the supply through resistors 11 and R1. A zener diode Z1 is placed between the minus terminal and the common point of the resistors 11 and R1 so as to maintain a constant voltage between these two points and thus minimize the variations in voltage at the terminals of the emitting diode (this avoids variation of the sensitivity as a function of the voltage of the battery). The bladder 6 and the screen 9 are disposed as before in the sealed chamber 5. The point common to the collector of the two transistors 7b is connected to the base of the transistor T1 whose collector is connected to the plus terminal of the supply through the resistor R2. The emitter of T1 is connected to the anode of a diode T1 whose cathode is connected to the minus terminal of the supply. A decoupling capacitor C1 is placed between the collector of T1 and the minus terminal of the supply, the collector of T1 being also connected to the input 5 of an integrated circuit having the reference CD 4538. For reasons of convenience, this circuit has been divided into two sub-assemblies CI1 and CI2 in the figure. Each of the two circuits CI1 and CI2 is a monostable circuit. The inputs 1 and 2 of CI1 are connected to the capacitor C2. The input 1 is also connected to the negative terminal of the supply and the input 2 is connected through a switch Cm1 to one of the resistors R71, R72 . . . R79 which may be chosen so as to obtain a time constant Rc corresponding to the duration of the pulse delivered by the monostable CI1 at its output 6 (output Q). The latter is connected to the input A (number 12) of CI2. The input B (number 11) of CI2 is connected to the output Q (number 9) of CI2, while the output Q of CI2 (number 10) is connected to the input 4 of CI1. Connected between the terminals 14 and 15 of CI2 is a circuit C3, and R3 for fixing the time constant of this monostable CI2. The input 15 is connected to the negative terminal of the supply and the input 4 is connected to the positive terminal through R3. The output Q of CI1 (number 7) is connected, on one hand, to the base of the transistor through the capacitor C5 connected in series with the resistor R5, and, on the other hand, to the base of the transistor T2 through the resistor R4. The emitters of the transistors T2 and T3 are connected to the negative terminal of the supply, and the collector of T2 is connected to the collector of T3 through the resistor R6. The collector of T3 is connected to one end of the winding L1 of the electrovalve V whose other end is connected to the positive terminal of the supply. A diode D4 also connects the collector of T3 to the positive terminal of the supply.

This device operates in the following manner. When the beam between the emitter 7b and the receiver 7a is interrupted at least partly by the strip 9 (see hereinafter the different modes of operation and the different adjustments which are possible), the receiver 7b is turned off and produces a rise in voltage at its collector, and therefore at the base of T1 which becomes conductive.

This results in a drop in potential at the collector of T1 and the passage to level O of the input 5 of CI1. This produces at the output Q of the monostable CI1 (number 6) the changing to level "1" of the latter which thus produces the actuation of the monostable CI2. Appearing at the output Q of the latter (number 10) is therefore a signal whose duration at level "1" will be a function of the time constant R3 C3 and which closes the input 4 of CI1. In this way it is possible to avoid the re-actuation of CI1 by a displacement of the strip 9 of the bladder 6 during a pre-determined period of time and thus ensure that the circuit does not oscillate and cause the opening and closing of the electrovalve EV at excessively short intervals of time. There therefore appears at the output $\bar{Q}$ of CI1 (number 7) the signal which is complementary to the signal appearing at Q, level "O". The transistor T2 is turned off. The electrovalve is no longer supplied with power (+ voltage at the collector of T3). The electrovalve EV is opened, since it concerns as electrovalve which is normally open in the absence of current for safety reasons. At the end of a period of time predetermined by C2 and Cm1, $\bar{Q}$ rises to state "1". The signal produces a pulse at the base of the transistor T3 after passing through the capacitor C5. This pulse saturates the transistor T3 which becomes conductive and thus produces an intense passage of current in the winding L1 of the electrovalve and consequently closes the latter. The closure is maintained by T2 which is conductive throughout the period of time during which $\bar{Q}$ is at level "1".

Figure 5:
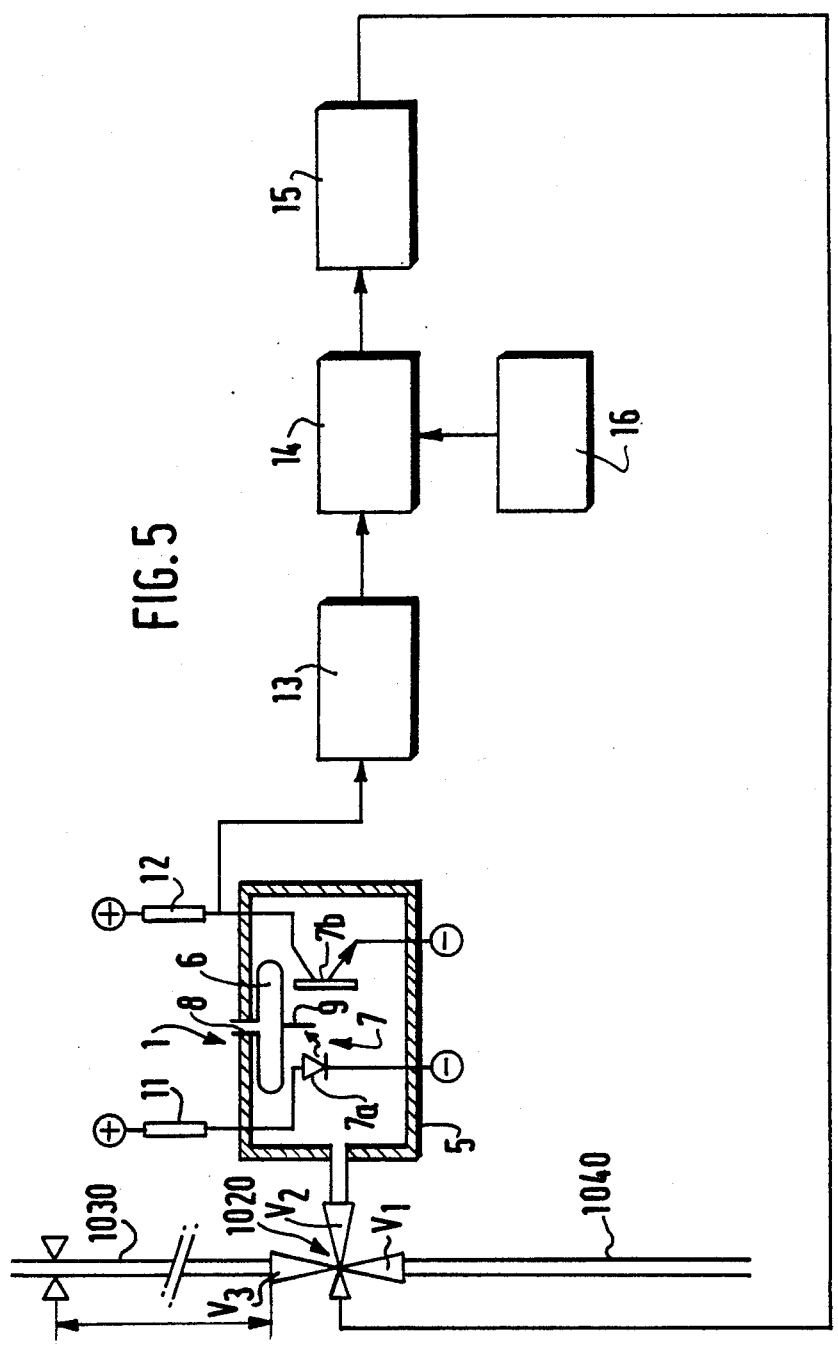
FIG. 5 shows a modification of FIG. 2 with a three-way electrovalve.

FIG. 5 illustrates a modification of the device shown in FIG. 2 with a three-way electrovalve. In this figure the same elements as those of the preceding figures carry the same reference numerals. The only element modified in this figure relative to FIG. 2 is the presence of the three-way electrovalve 1020. In this mode of operation, the oxygen coming from a source (not shown in the drawings) is delivered to the patient through the pipe 1030, then the electrovalve 1020 and finally the pipe 1040 which opens onto the nostrils of the patient. The threeway electrovalve 1020 ensures that a pressure is not sent into the detector 1 at the beginning of inhaling. When the patient inhales through 1040, the ways V1 and V2 are opened and then put into communication with each other which produces a slight depression in the sensor 1 therefore triggering through the circuit 13,14,15,and 16, the opening of the electrovalve 1020, i.e. the communication of the way V3 with the way V1 without communication of the way V3 with the way V2. In this way it is ensured that the operation of the sensor is not disturbed by the delivery of a pressure at the beginning of the inhaling phase.

Figure 6:
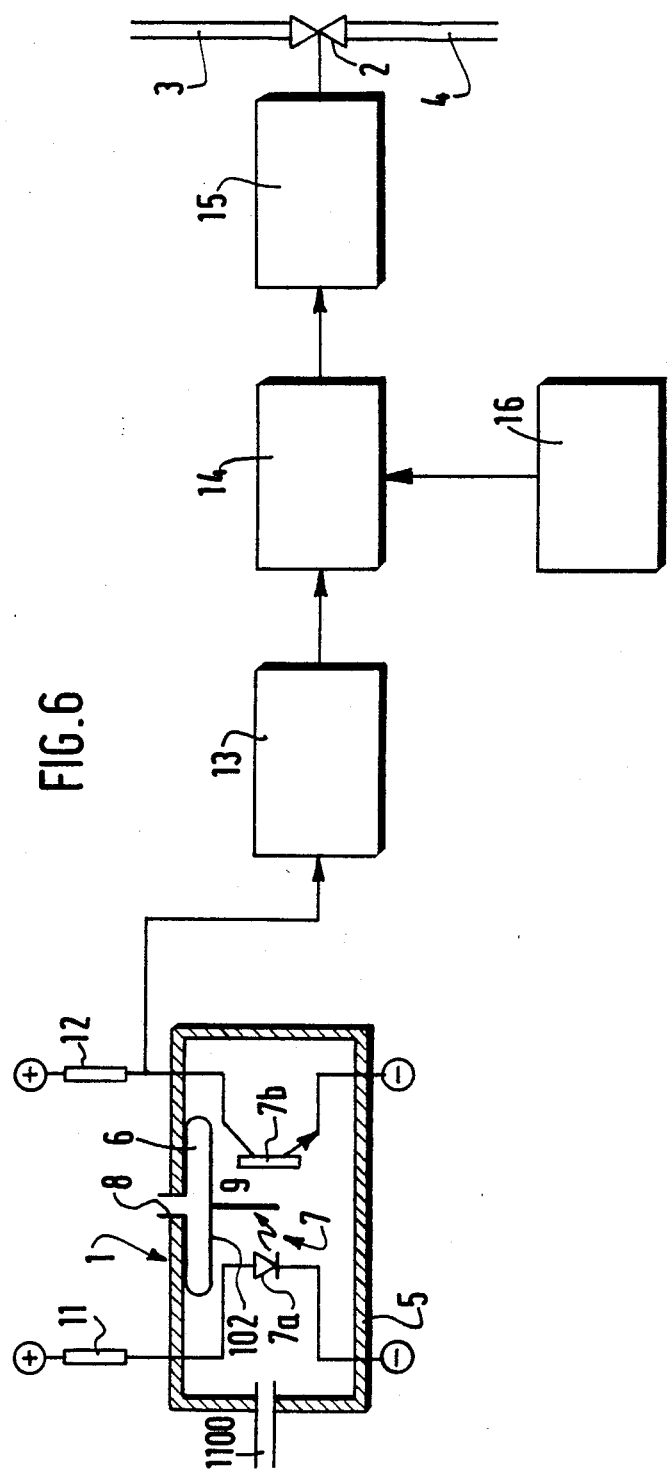
FIG. 6 is an embodiment of a system with actuation at the end of the exhaling phase.

FIG. 6 shows a modification of the invention with a system triggering at the end of exhaling. Indeed, in the devices described hereinbefore, the inhaling effort of the patient was always used for initiating the blowing of the oxygen or of the gaseous mixture. However, in some applications it has been found that the response time of the electronic and mechanical system may be rather long and exceed 100 and even 200 milliseconds. Indeed, this response time depends partly on the inhaling effort of the patient and will be all the longer if this effort is weak. At the start of the inhaling, the first gas to enter the pulmonary alveoli during the inhaling is the alveolar gas which filled the dead anatomical space at the end of the preceding exhalation. It is very important to ensure that the oxygen can reach the alveoli right from the start of the inhalation. It is even desirable to replace the alveolar gas which filled the dead space at the end of the previous exhalation.

In order to improve the operation of the sensor described hereinbefore, the system of the present modification is such that it is no longer the inhalation which starts up the system but the end of the exhalation of the patient, when there is no longer an exhalation flow. The starting up therefore occurs during the pre-inhalation period which permits, bearing in mind the delays, a supply of oxygen right at the start of the inhaling phase of the patient or even before, which is advantageous since a part of the dead space would then contain the oxygen mixture and not the alveolar gas.

To use the system according to this modification, it is merely necessary to modify the setting of the sensor 1. In this case, the position of rest of the strip 9 in which it interrupts or intercepts completely or partly the light beam between 7a and 7b, corresponds to the opening of the oxygen supply valve, or more precisely to the inhaling phase of the patient. Right at the start of the exhalation phase of the patient, the exhalation gas which reaches the detector 1 through the pipe 110 causes an increase in pressure through the detector 1, this increase in pressure producing a force on the lower side 102 of the bladder 6 which starts the raising of the strip 9. The light beam between 7a and 7b is no longer intercepted by the strip 9. The sending of a level "1" to the input 5 of the monostable CI2 is without effect. As soon as the exhaling effort of the patient ceases, i.e. when there is not longer any exhaling flow, the strip descends and intercepts the infrared beam. The point A becomes positive (transistor 7b is turned off) which causes, in the manner explained in FIG. 4, the opening of the electrovalve EV and the blowing of oxygen during the predetermined period of time. Of course, the use of such a process described with reference to FIG. 5 is not limited to oxygen treatment and to this type of sensor. It can be applicable in any field where it is preferable to anticipate the starting up of the inhalation cycle so as to deliver the gaseous mixture in a pre-inhalation period or right at the start of the inhalation of the patient.

FIG. 7 shows a detailed view of an embodiment of a device according to the invention. The bladder 6 has a planar lower side 102 to which the strip 9 is fixed, for example by an adhesive. This side 102 is extended by two lateral surfaces.

FIG. 7 shows different views of an embodiment of a device according to the invention.

Figure 7A:
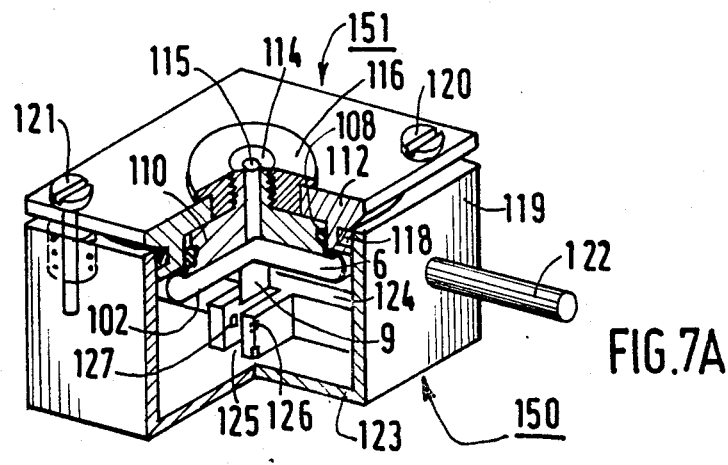
FIG. 7 is a detailed view of an embodiment of a device according to the invention.
Figure 7C:
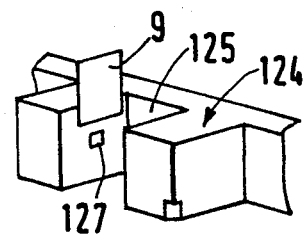

FIG. 7A is a partial sectional view of the device according to the invention. This device comprises a case formed by a base 150 and a cover 151 connected together by screws 120 and 121 which permit the adjustment in height of the cover 151 relative to the base 150, springs (not shown in the drawing) being interposed between the base and the cover for exerting an upward force.

Disposed in the base 150 having a lower wall 123 and lateral walls 119, is an opto-electronic device 124 mainly comprising a slot 125 with an emitter 127 and a receive 126 (or vice versa) disposed on each side of the slot. The cover 151, shown in section in FIG. 7b, comprises the cover proper 112 in which is inserted the bladder support 110 which is connected to the cover 112 by an upper member 116 which is screwed around the screw thread 114 projecting from the center of the support 110. The member 116 bears by its circular bearing surface 117 against the cylindrical opening in the cover 112, the support 110 abutting by its upper part against the circular inner bearing surface 113 of the cover 112. The bladder 6 is connected to the support 110 by the fixing of its annular part 106 in the groove 108. The part 107 of the bladder above 106 acts as a sealing element in the region of the circular bearing surface 113. The bladder 6 is extended beyond its vertical cylindrical part 106,107 by a horizontal circular ring 104. The latter is extended, when viewed in section, by a semi-circular part 101 which is extended by a circular planar surface 102. The strip 9 is connected to the surface 102, substantially in the center of the latter.

This device operates in the following manner.

The bladder 6 communicates with the exterior atmosphere through the passage 115 provided in the support 110. The air therefore exerts a force on the side 102A of the bladder 6. The outer side of the bladder is in contact with the exhaled air and/or inhaled air of the patient which reaches the detector 1 through the pipe 122, the chamber being maintained in the sealed state by the O-ring 118. This "patient" air exerts an opposing force on the side 102B.

Figure 7D:
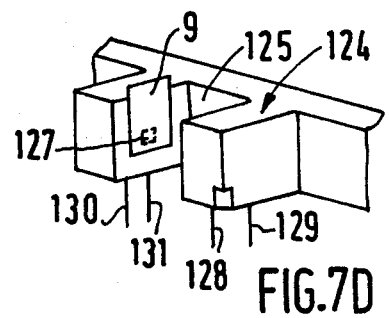
Figure 7B:
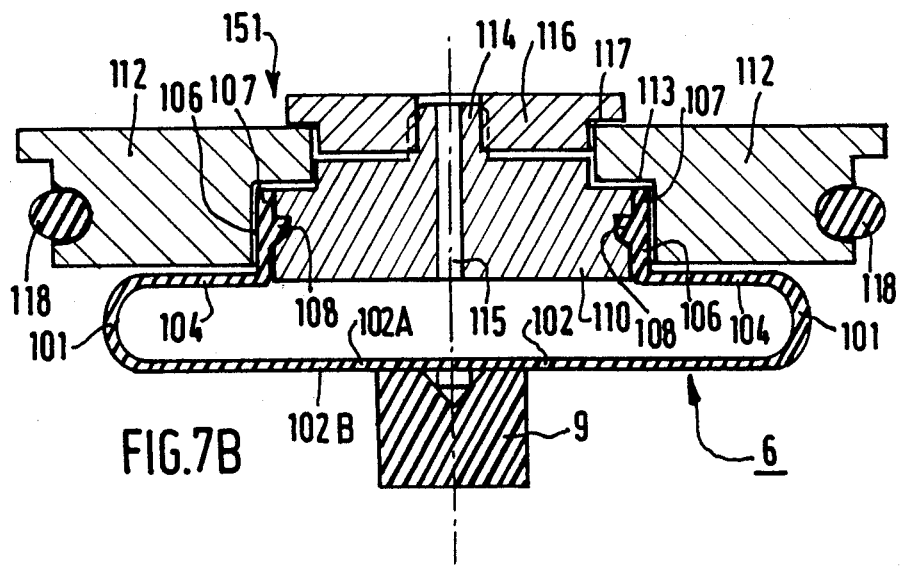

When the pressure of the "patient" air in the chamber 1 is equal to atmospheric pressure, the strip 9 does not intercept the light beam between 126 and 127 (for example in the FIG. 7C) when the patient creates a depression in the chamber (inhalation)—FIG. 7D, the strip intercepts all or part of the beam (according to the setting), the force exerted by the surrounding air on 102A being greater than that exerted by the "patient" air and deforming the diaphragm 102 (the latter becomes convex). Inversely, in the course of exhalation, the "patient" air in the chamber 1 is at a pressure higher than the surrounding air and the diaphragm 102 is urged upwardly (it assumes a concave shape) and the strip no longer intercepts the beam.

The fact that there are three possible positions for the diaphragm 102 (planar, concave, convex) may be used for an operation described with reference to FIG. 6. When the diaphragm 102 is at rest (planar), the strip intercepts the beam—when the patient inhales, the strip no longer completely (or partly) intercepts the beam. At the end of the inhalation, the pressure in the chamber increases, the strip then intercepts the beam partly (or completely, depending on the setting of the electronic circuit) and the electronic circuit of FIG. 4 is actuated so as to open the oxygen electrovalve. The emitter 7a and the receiver 7b are respectively connected (FIG. 4) by the electric connections 130, 131 and 128, 129.

Although in the foregoing description there was principally considered the application of the depression detector to oxygen treatment, it will be understood that it may be used in any field requiring the detection of depressions lower than 0.1 millibar and that it may also be used whenever it is necessary to detect small differential pressures, i.e. small variations in pressure with respect to a reference pressure.

The detector according to the invention is particularly useful in connection with the apparatus disclosed in U.S. Pat. Application Ser. No. 507,467, Robert et al, incorporated herein as a reference, substituting in said apparatus the thermistor detectors and their corresponding electronic circuit for the detector according to the invention and its corresponding electronic circuit. The apparatus is thus more reliable and oxygen injection can be activated either at the end of exhalation phase or at the beginning of inhalation phase.

What is claimed is:

1. A device for treating respiratory deficiency of a patient by the supply of an inhalation fluid from a source of inhalation fluid to supplement the supply of oxygen inhaled from the surrounding atmosphere by the patient, the device comprising a first duct, means to connect one end of said first duct to said source of inhalation fluid, valve means in said first duct adapted to control the flow of inhalation fluid through said duct from said source of inhalation fluid, a chamber having an opening, a second duct having a plurality of outlets, means to connect one of the outlets of said second duct to the opening of said chamber, means to connect another outlet of said second duct to the valve means to control the flow of inhalation fluid, a third outlet of said second duct being adapted for insertion into the patient, a reservoir in the form of a pliable bladder within the chamber and having a pressure responsive movable wall, an electronic circuit connected to the valve means to control the same, said electronic circuit including monostable means for producing a digital output signal, a photodetector unit connected to the electronic circuit and including means for emitting a light beam, means for receiving said light beam and means for intercepting the light beam dependent on said movable wall, said reservoir having an opening communicating with the surrounding atmosphere, said movable wall being subjected on one side to the pressure of air from the surrounding atmosphere and on the other side to the pressure of the fluid to or from the patient, the difference of pressure between the two sides of the movable wall causing a displacement of said wall in a direction toward the lower pressure, said wall moving toward said light beam when the pressure on one side of the wall exceeds that on the other side to position the intercepting means in intercepting relationship with said beam, said wall moving away from said light beam when the pressure on said other side of said wall exceeds that on said one side to position said intercepting means at a remote location with respect to said beam.

2. A device according to claim 1, wherein said means for intercepting the light beam is a screen directly fastened to the movable wall of the reservoir.

3. A device according to claim 2, wherein the bladder is made of a material having a pliability such that a pressure variation of one millimeter of water on a side of the movable wall results in a displacement of the screen of at least 0.05 mm.

4. A device according to claim 2, wherein the screen does not noticeably intercept the light beam when the valve means are closed and the second duct is not in communication with the patient.

5. A device according to claim 2, wherein the screen noticeably intercepts the light beam when the valve means are closed and the second duct is not in communication with the patient.

6. A device according to claim 2, wherein the chamber comprises adjustment means for adjusting the screen relative to the light beam.

7. A device according to claim 1 or 2, wherein the inhalation fluid is oxygen.

8. A device according to claim 1, wherein the means for intercepting the light beam is adjusted relative to said light beam in such a way that said intercepting means at least partly intercepts said light beam during the inhalation phase of the patient and no more than partly intercepts said light beam during the exhalation phase of the patient, said intercepting means no longer intercepting said light beam when the pressure is the same on both sides of the movable wall, the means for intercepting the light beam generating a signal to the valve means to open the same at the beginning of the inhalation phase and to close the same at the end of said inhalation phase.

9. A device according to claim 1, wherein the means for intercepting the light beam is adjusted relative to said light beam in such a way that said intercepting means at least partly intercepts said light beam during the inhalation phase of the patient and no more than partly intercepts said light beam during the exhalation phase of the patient, said intercepting means at least partly intercepting said beam when the pressure is the same on both sides of the movable wall, the photodetector unit generating a signal to the valve means to open the same at the end of the exhalation phase and to close the same at the beginning of the exhalation phase.

10. A device according to claim 2, wherein said means for intercepting the light beam at least partly intercepts the light beam when the pressure is the same on both sides of the movable wall and no more than partly intercepts the light beam when the pressure in the reservoir is lower than in the chamber.

11. A device according to claim 1, wherein said means for intercepting the light beam no more than partly intercepts the light beam when the pressure is the same on both sides of the movable wall and at least partly intercepts the light beam when the pressure in the reservoir is higher than in the chamber.

12. A device for treating respiratory deficiency of a patient by the supply of an inhalation fluid from a source of inhalation fluid to supplement the supply of oxygen inhaled from the surrounding atmosphere by the patient, the device comprising a first duct, means to connect one end of said first duct to said source of inhalation fluid, valve means in said first duct adapted to control the flow on inhalation fluid through said duct from said source of inhalation fluid, a chamber having an opening, a second duct having two outlets, means to connect one of the outlets of said second duct to the valve means to control the flow of inhalation fluid, means to connect the other outlet of said second duct to the patient, an accessory take-off pipe having two ends, one end adapted for insertion into the patient, means adapted to connect the other end of said accessory take-off pipe to the opening of said chamber, a reservoir in the form of a pliable bladder within the chamber and having a pressure responsive movable wall, an electronic circuit connected to the valve means to control the same, said electronic circuit including monostable means for producing a digital output signal, a photodetector unit connected to the electronic circuit and including means for emitting a light beam, means for receiving said light beam and means for intercepting the light beam dependent on said movable wall, said reservoir having an opening communicating with the surrounding atmosphere, said movable wall being subjected on one side to the pressure of air from the surrounding atmosphere and on the other side to the pressure of air to or from the patient, the difference of pressure between the two sides of the movable wall causing a displacement of said wall in a direction toward the lower pressure, said wall moving toward said light beam when the pressure on one side of the wall exceeds that on the other side to position the intercepting means in intercepting relationship with said beam, said wall moving away from said light beam when the pressure on said other side of said wall exceeds that on said one side to position said intercepting means at a remote location with respect to said beam.

13. A device according to claim 12, wherein the electronic circuit comprises a shaping circuit connected to the electronic control circuit, said photodetector unit producing output pulses which are shaped by said shaping circuit, means for applying the output pulses to the control circuit to control the valve means so as to maintain it open so long as a depression prevails in said take-off pipe.

14. A device for treating respiratory deficiency of a patient by the supply of an inhalation fluid from a source of inhalation fluid to supplement the supply of oxygen inhaled from the surrounding atmosphere by the patient, the device comprising a first duct, means to connect one end of said first duct to said source of inhalation fluid, three-way valve means with three outlets, means to connect the other end of said first duct to the first outlet of said valve means, a chamber having an opening, a second duct, means to connect one outlet of said second duct to a second outlet of said valve means, means to connect another outlet of said second duct to the opening of said chamber, a third duct, means to connect one end of said third duct to the third outlet of said valve means, the second end of said third duct being adapted for insertion into the patient, a reservoir in the form of a pliable bladder within the chamber and having a pressure responsive movable wall, an electronic circuit connected to the valve means to control the same, said electronic circuit including nonostable means for producing a digital output signal, a photodetector unit connected to the electronic circuit and including means for emitting a light beam, means for receiving said light beam and means for intercepting the light beam dependent on said movable wall, said reservoir having an opening communicating with the surrounding atmosphere, said movable wall being subjected on one side to the pressure of air from the surrounding atmosphere and on the other side to the pressure of air to or from the patient, the difference of pressure between the two sides of the movable wall causing a displacement of said wall in a direction toward the lower pressure, said wall moving toward said light beam when the pressure on one side of the wall exceeds that on the other side to position the intercepting means in intercepting relationship with said beam, said wall moving away from said light beam when the pressure on said other side of said wall exceeds that on said one side to position said intercepting means at a remote location with respect to said beam.

15. A device according to claim 14, wherein said means for intercepting the light beam at least partly intercepts the light beam when the pressure is the same on both sides of the movable wall and no more than partly intercepts the light beam when the pressure in the reservoir is lower than in the chamber.

16. A device according to claim 14, wherein said means for intercepting the light beam no more than partly intercepts the light beam when the pressure is the same on both sides of the movable wall and at least partly intercepts the light beam when the pressure in the reservoir is higher than in the chamber.

17. A device for treating respiratory deficiency of a patient by the supply of an inhalation fluid from a source of inhalation fluid to supplement the supply of oxygen inhaled from the surrounding atmosphere by the patient, the device comprising a first duct, means to connect one end of said first duct to said source of inhalation fluid, valve means in said first duct adapted to control the flow of inhalation fluid through said duct form said source of inhalation fluid, a chamber having an opening communicating with the surrounding atmosphere, a reservoir in the form of a pliable bladder within the chamber and having an opening and a pressure responsive movable wall, a second duct having a plurality of outlets, means to connect one of the outlets of said second duct to the opening of said reservoir, means to connect another outlet of said second duct to the valve means to control the flow of inhalation fluid, a third outlet of said second duct being adapted for insertion into the patient, an electronic circuit connected to the valve means to control the same, said electronic circuit including monostable means for producing a digital output signal, a photodetector unit connected to the electronic circuit and including means for emitting a light beam, means for receiving said light beam and means for intercepting the light beam dependent on said movable wall, said movable wall being subjected on one side to the pressure of air from the surrounding atmosphere and on the other side to the pressure of the fluid to or from the patient, the difference of pressure between the two sides of the movable wall causing a displacement of said wall in a direction toward the lower pressure, said wall moving toward said light beam when the pressure on one side of the wall exceeds that on the other side to position the intercepting means in intercepting relationship with said beam, said wall moving away from said light beam when the pressure on said other side of said wall exceeds that on said one side to position said intercepting means at a remote location with respect to said beam.

18. A device according to claim 17, wherein said means for intercepting the light beam no more than partly intercepts the light beam when the pressure is the same on both sides of the movable wall and at least partly intercepts the light beam when the pressure in the reservoir is higher than in the chamber.

19. A device according to claim 17, wherein said means for intercepting the light beam at least partly intercepts the light beam when the pressure is the same on both sides of the movable wall and no more than partly intercepts the light beam when the pressure in the reservoir is lower than in the chamber.

20. A pressure responsive device comprising a chamber having a first opening, a reservoir in the form of a pliable bladder within the chamber and having a pressure responsive movable wall and having a second opening, duct means supplied with fluid under pressure, means for connecting the duct means to one of said openings, the other opening communicating with the surrounding atmosphere, valve means interposed in the duct means for controlling the flow of fluid therethrough, an electronic circuit connected to the valve means to control the same, said electronic circuit including monostable means for producing a digital output signal, a photodetector unit connected to the electronic circuit and including means for emitting a light beam and means for receiving said light beam, means for intercepting said light beam in the form of a screen movable in response to movement of said movable wall, the difference in pressure between the two sides of the movable wall causing a displacement of said wall in the direction of the lower pressure, said wall moving toward said light beam when the pressure on one side of the wall exceeds that on the other side to position said screen in intercepting relationship with said beam, said wall moving away from said light beam when the pressure on said other side of said wall exceeds that on said one side to position said screen at a remote location with respect to said beam.

21. A device according to claim 20, further comprising means for adjusting the screen relative to the light beam to adjust the position of the screen when the pressure is the same on the two sides of the movable wall.

22. A device for treating respiratory deficiency of a patient according to claim 20, wherein the second gas is fluid to or from the patient.

* * * * *